(12) United States Patent
Plicchi et al.

(10) Patent No.: US 6,240,314 B1
(45) Date of Patent: May 29, 2001

(54) HEART STIMULATION DEVICE WITH ELECTROTONIC INHIBITION

(75) Inventors: Gianni Plicchi, Bologna; Bruno Garberoglio, Turin; Guido Gaggini, Milan; Emanuela Marcelli, Macerata, all of (IT)

(73) Assignee: Sorin Biomedica Cardio S.p.A. (IT)

( * ) Notice: Subject to any disclaimer, the term of this patent is extended or adjusted under 35 U.S.C. 154(b) by 0 days.

(21) Appl. No.: 09/301,372

(22) Filed: Apr. 26, 1999

(30) Foreign Application Priority Data

Jan. 28, 1999 (EP) .................................................. 99830035

(51) Int. Cl.[7] .................................................. A61N 1/365
(52) U.S. Cl. .................................................. 607/14
(58) Field of Search .................................. 607/9, 13, 14, 607/4, 5

(56) References Cited

U.S. PATENT DOCUMENTS

| | | |
|---|---|---|
| 5,083,564 | 1/1992 | Scherlag . |
| 5,800,464 | 9/1998 | Kieval . |

FOREIGN PATENT DOCUMENTS

| | | |
|---|---|---|
| 0 813 889 A2 | 12/1997 | (EP) . |
| 0 813 889 A3 | 12/1997 | (EP) . |

OTHER PUBLICATIONS

Davidenko et al., "Electrotonic Inhibition and Active Facilitation of Excitability in Ventricular Muscle," *Journal of Cardiovascular Electrophysiology*, 5(11):945–960 (Nov. 1994).
Fromer et al., "Ultrarapid Subthreshold Stimulation for Termination of Atrioventricular Node Reentrant Tachycardia," *JACC*, 20(4):879–883 (Oct. 1992).
Garrigue et al., "Post–Ganglionic Vagal Stimulation of the Atrioventricular Node Reduces Ventricular Rate During Atrial Fibrillation," *PACE*, 21(4):878 (Part II) (Apr. 1998).
Meijler et al., "AV Nodal Function During Atrial Fibrillation: The Role of Electrotonic Modulation of Propagation," *Journal of Cardiovascular Electrophysiology*, 7(9):843–861 (Sep. 1996).
Meijler et al., "On the Mechanism(s) of Atrioventricular Nodal Transmission in Atrial Fibrillation," *CARDIOLOGIA*, 42(4):375–384 (1997).
Willems et al., "Subthreshold Stimulation in the Region of the Slow Pathway During Atrioventricular Node Reentrant Tachycardia: Correlation With Effect of Radiofrequency Catheter Ablation," *JACC*, 29(2):408–415 (Feb. 1997).
Windle et al., "Subthreshold Conditioning Stimuli Prolong Human Ventricular Refractoriness," *The American Journal of CARDIOLOGY*, 57(6):381–386 (Feb. 15, 1986).
PCT Notification of Transmittal of the International Search Report for EP 99 83 0035.

*Primary Examiner*—Scott M. Getzow
(74) *Attorney, Agent, or Firm*—Popovich & Wiles, PA

(57) ABSTRACT

Electrodes can generate electrical stimulation pulses at least one first intensity level and at least one second intensity level. The first and second intensity levels are above and below a given stimulation threshold, respectively. The synchronous or asynchronous delivery of second-level pulses enables the conduction of the atrioventricular node to be modulated by electrotonic effect, for example, to reduce ventricular frequency in the event of atrial fibrillation.

14 Claims, 2 Drawing Sheets

HEART STIMULATION DEVICE WITH ELECTROTONIC INHIBITION

FIELD OF THE INVENTION

The present invention relates to a device and a method for electrical stimulation of the heart.

BACKGROUND OF THE INVENTION

Experimental studies on animals and on man (such as those reported, for example, in the work "Electronic inhibition and active facilitation of excitability in ventricular muscle" by J. M. Davidenko, M. Delmar, and J. Beaumont in J. Cardiov. Electrophysiol. Vol. 5, No. 11 November 1994, pages 945–960), have shown the effects of subthreshold electrical stimuli on response to subsequent stimulations. These effects are referred to briefly by the term electrotonic inhibition. According to this research, the introduction of a subthreshold conditioning stimulus between two above-threshold stimulations is followed by a transitory decay in the excitability of the muscle stimulated. In particular, a subthreshold stimulus triggered a certain period of time before the subsequent above-threshold stimulus may delay the response to the subsequent stimulus in question, increasing so-called latency, that is, the interval between the pulse and the respective rapid front of the action potential, and even having an actual inhibition effect. The degree of inhibition is directly proportional to the amplitude and to the duration of the subthreshold conditioning stimulus and is inversely proportional to the post-conditioning period between the electrotonic inhibition pulse and the next stimulation pulse.

Electrotonic inhibition can explain some phenomena which occur during atrial fibrillation in man. This applies in particular to the paradoxical effect of a reduction in ventricular frequency due to the action of a vagotonic drug such as digitalis (which reduces atrial refractory periods and therefore considerably increases the frequency of local atrial fibrillation) and to the effect observed, also during atrial fibrillation, of a reduction in the shortest R-R periods of the electrocardiograph signal, to the point of disappearance, when the ventricle is stimulated at longer intervals.

These phenomena can be explained only by electrotonic inhibition which would act on the atrioventricular node, actually reducing its conduction rate as a result of the increased atrial fibrillation frequency and because of the reverse conduction of ventricular stimuli.

In this connection, the following references may be consulted: "On the mechanism(s) of atrioventricular nodal transmission in atrial fibrillation" by F. L. Meijler and J. Jalife in Cardiology 1997; 42(4); pages 375–384, and "AV nodal function during atrial fibrillation; the role of electrotonic modulation of propagation" by F. L. Meijler, J. Jalife, J. Beaumont, and D. Vaidya in J. Cardiov. Electrophysiol. Vol. 7, No. 9 September 1996, pages 843–861.

Recent tests in which subthreshold stimuli were used to terminate re-entrant ventricular tachycardia, both at local level and by involving the atrioventricular node, with a view to evaluating the optimal site for performing a radio frequency ablation, should also be considered as further support for the hypothesis of the effect of a reduction in the propagation rate and of an extension of the refractory period. The following references should also be referred to in this connection:

"Subthreshold conditioning stimuli prolong human ventricular refractoriness" by J. R. Windle, W. M. Miles, D. P. Zipes, and E. N. Prystowsky, in Am. J. Cardiol. 1986; 57; pages 381–6, and "Subthreshold stimulation in the region of the slow pathway during atrioventricular node re-entrant tachycardia: correlation with effect of radio-frequency catheter ablation" by S. Willems, C. Weiis, T. Hofmann, C. Rickers, and T. Meinertz in JACC Vol. 29, No. 2, February 1997, pages 408–15.

SUMMARY OF THE INVENTION

The object of the present invention is to provide improved solutions which can take advantage of the above-described phenomenon, known as electrotonic inhibition, to achieve an improvement in the course of the electrical heart-stimulation effect.

In one aspect, this invention is a heart-stimulation device comprising first stimulator means for applying electrical stimulation pulses at a first intensity level; second stimulator means for applying electrical stimulation pulses at a second intensity level; the first and second intensity levels being above and below a stimulation threshold, respectively; control means in electrical communication with the first and second stimulator means and capable of selectively controlling the generation of the stimulation pulses in the first and second stimulator means at the first intensity level and at the second intensity level. Preferably, the first stimulator means and the second stimulator means are configured to stimulate distinct regions of the heart. The first stimulator means may stimulate at least one of an atrial region and a ventricular region, and the second stimulator means may stimulate the heart muscle in the region of the atrioventricular node. The second stimulator means may further comprise sensing means for sensing the activity of the heart muscle. The control means can vary selectively at least one intensity parameter selected from the group of pulse amplitude, duration and frequency. The second stimulator means may be configured to generate a sub-threshold stimulation pulse in the form of individual pulses or repeated pulse trains and/or the pulse may synchronous or asynchronous with spontaneous heart activity.

In another aspect, this invention is an electrical heart-stimulation device comprising a first electrode adapted to apply electrical stimulation pulses at a first intensity level; a second electrode adapted to apply electrical stimulation pulses at a second intensity level; the first and second intensity levels being above and below a stimulation threshold, respectively; a processing unit in electrical communication with the first and second electrode, the processing unit capable of selectively controlling the generation of the electrical stimulation pulses in the first and second electrodes at the first intensity level and at the second intensity level.

In yet another aspect, this invention is a method of stimulating the heart, comprising providing a processing unit in electrical communication with a means for detecting atrial fibrillation and with first and second electrodes; implanting the electrodes in the heart; providing electrical stimulation pulses to the heart from the first electrode above a stimulation threshold; and providing electrical stimulation pulses to the heart from the second electrode below a stimulation threshold, wherein the electrical stimulation pulses are delivered in response to the detection of atrial fibrillation.

DETAILED DESCRIPTION OF PREFERRED EMBODIMENTS

It should be noted that, in the current state of the art, only sporadic use of antitachycardia electrical stimulators temporarily programmed to deliver trains of subthreshold pulses in order to terminate re-entrant atrioventricular tachycardia is known; reference should be made in particular to the work "Ultra rapid subthreshold stimulation for termination of atrioventricular node re-entrant tachycardia" by M. Fromer and M. Shenasa, in JACC Vol. 20, No. 4, October 1992, pages 879–83.

Specific applications for the control of ventricular frequency during atrial fibrillation in particular are not known.

The apparatus of this invention can be configured, in the currently-preferred embodiment, as a dual chamber electrical stimulator which applies the methods bringing about electrotonic inhibition. This stimulator is particularly effective for the treatment of chronic or paroxysmal atrial fibrillation in patients in whom pharmacological control of ventricular frequency is difficult and in whom it is not possible or is not intended to perform permanent ablation.

The dual-chamber stimulator is of an advanced type and any currently-known solution, particularly multi-pole stimulation of the right atrium or biatrial stimulation, may be used for preventing atrial fibrillation.

In a preferred embodiment, the stimulator has an associated stimulation/sensing channel which can be dedicated independently to bringing about the electrotonic inhibition effect, preferably applied to the atrioventricular node. For this purpose, an electrode located chronically in the vicinity of this node can deliver stimuli of programmable amplitude, duration and frequency when a situation of atrial fibrillation is detected.

The stimuli may be asynchronous or synchronous with local electrophysiological activity, with provision for capture between two successive physiological activations. The stimulation frequency may be adjusted by means of an algorithm (known per se) which can take account of the ventricular period.

The electrotonic effect may be controlled by subthreshold pulses or pulses which are effective with reference to the arrangement of the electrode dedicated to this function. The electrode used has characteristics of low polarization and is associated with amplifier circuits which can operate with the local electrograms originated during atrial fibrillation, in which electrogram frequencies of 300–600 per minute are common.

The invention will now be described, purely by way of non-limiting example, with reference to the Figures.

Figure 1:
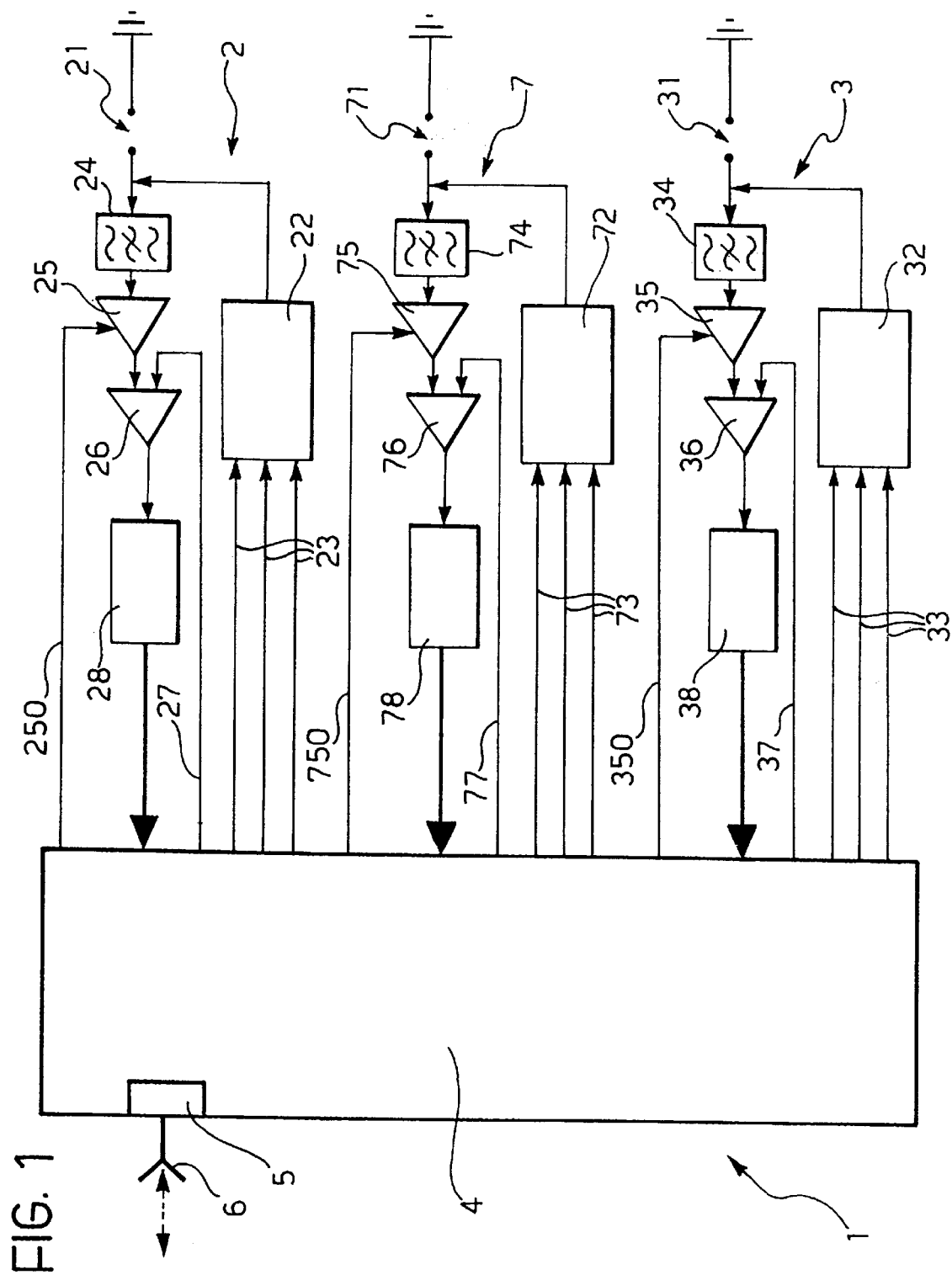
FIG. 1 shows a block diagram of an electrical heart-stimulator device of the present invention.

In FIG. 1, a device, generally indicated 1, is substantially comparable to a normal electrical atrioventricular stimulator and, according to the invention, has a supplementary module which can perform an electrotonic inhibition function. In particular, the set of circuit components—which can be considered generally known—form the means for bringing about the stimulation effect at the atrial level and at the ventricular level (i.e., generally indicated 2 and 3, respectively).

In particular, respective stimulation electrodes, indicated 21 and 31, are driven, in order to provide stimulation pulses, by respective power stages 22 and 32. These in turn are controlled by processing and timing unit 4, by means of respective sets of lines, indicated 23 and 33, (each set usually being constituted by a synchronization or trigger line, an amplitude-control line and a duration-control line). Unit 4 usually has telemetering module 5 with associated respective antenna means 6, to permit bidirectional remote exchange of data.

In this connection, it will be appreciated that the whole device indicated 1 is configured in general in a manner such that it can be implanted in the patient's body.

Each of electrodes 21 and 31 is also connected to processing and timing unit 4 by means of a so-called "sensing" line comprising, in series, filter 24, 34, for rejecting interference and spurious signals, and amplifier 25, 35 the gain of which is determined selectively by processing and timing unit 4 by means of atrial or ventricular gain-control line 250 or 350, respectively. The sensing signal coming from each amplifier 25 and 35 is compared, in a respective threshold comparator, indicated 26 or 36, with a threshold level set by processing and timing unit 4, by means of respective line 27 or 37.

Finally, respective detectors 28 and 38—of known type—can detect the value of the so-called "A" period (atrial period) and of the so-called "V" period (ventricular period) in dependence on the output signal of threshold comparators 26 and 36, generating corresponding—usually digital—signals for transmission to processing and timing unit 4 for processing and for bringing about a feedback effect on the driving of the stimulation.

The solution according to the invention is characterized by the presence of a further stimulation and sensing channel, generally indicated 7, which provides a pulse below the stimulation threshold. This channel is substantially similar to channels 2 and 3 described above. It thus comprises electrode 71 to be implanted in the heart muscle in the vicinity of the atrioventricular sinus in order to bring about an electrotonic stimulation effect at that site, in dependence on a driving signal generated by power stage 72.

Power stage 72 is driven by processing and timing unit 4 in substantially the same manner as stages 22 and 32, by means of a set of respective synchronizing (trigger), amplitude-control and duration-control lines 73. In particular, processing and timing unit 4 can impart to power stage 72, by means of lines 73, control and stimulation signals such as to give rise, by means of electrode 71, either to isolated subthreshold signals with a frequency comparable to the heart frequency, or to very rapid and repeated pulse trains. By way of example, one of these pulse trains may comprise, for example, 20 pulses at a frequency corresponding to 400 pulses per minute, these pulse trains possibly even being repeated tens of times.

In one embodiment of the invention, the above-mentioned pulse trains have a duration of the order of about 150 ms with a pulse-train repetition frequency of about 120 bpm (beats per minute). An individual pulse typically has a duration of the order of about 1 ms, with a subthreshold amplitude, for example, of around 0.1 volt. Naturally, this amplitude value may be rendered variable selectively in dependence on specific requirements of use. The frequency of repetition of the pulses within an individual train is preferably of the order of about 120 hertz.

With regard to the structure of the sensing line, channel 7 is also structurally similar to channels 2 and 3 described above. In particular, a filter for rejecting interference and spurious signals and an amplifier, the gain of which is controlled by processing and timing unit 4 by means of line 750, are indicated 74 and 75.

A threshold comparator in which the output signal of amplifier 75 is compared with a threshold level transmitted by processing and timing unit 4 on line 77 is indicated 76. The result of the comparison is transmitted to detector 78 which identifies the duration of the so-called "AVJ" period, that is, the period of the signal detected by electrode 71 at its implantation site, and which transmits a corresponding signal to processing and timing unit 4.

Figure 2:
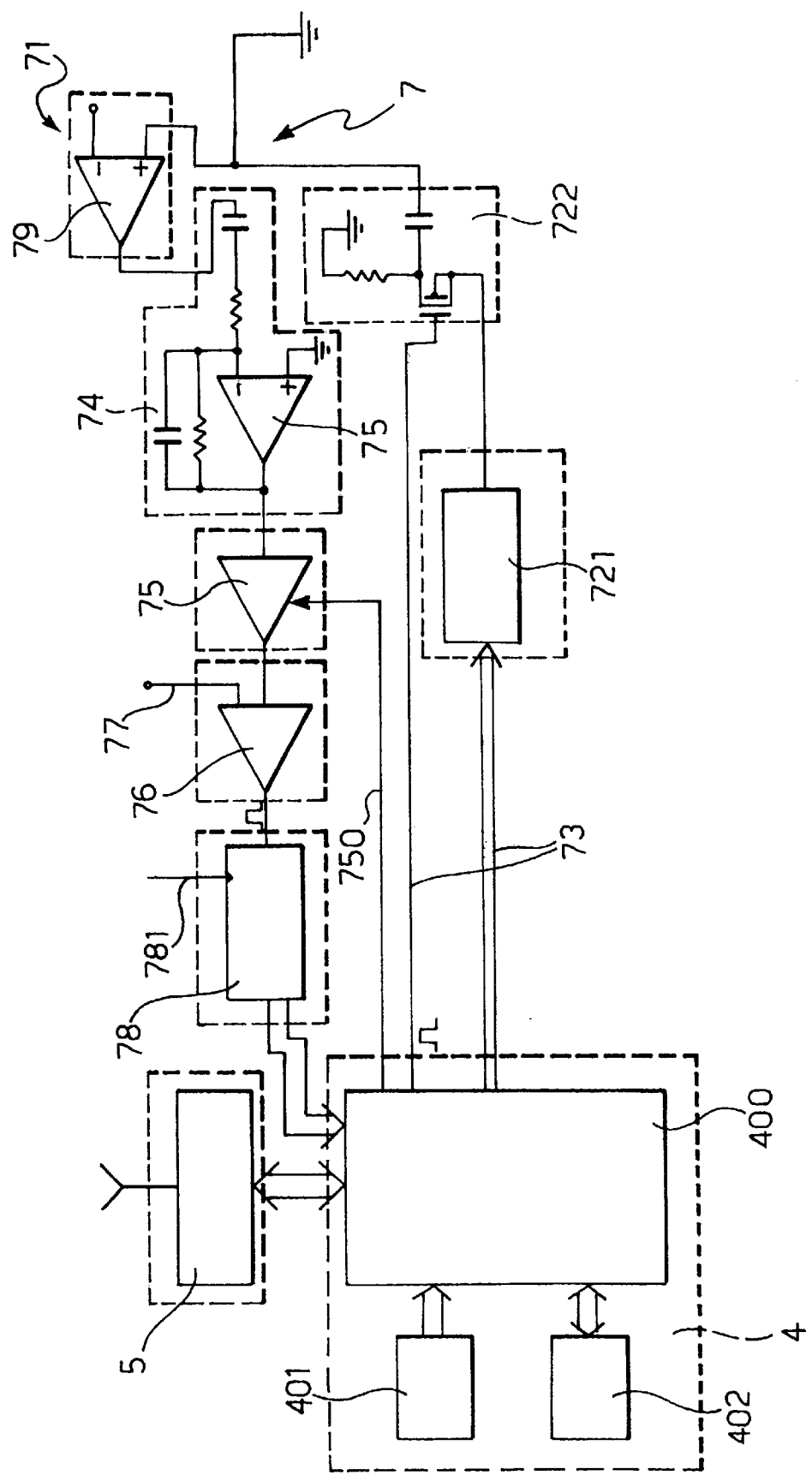
FIG. 2 shows a portion of the device of FIG. 1 in greater detail.

The diagram of FIG. 2 shows channel 7 of the device shown in FIG. 1 with even more circuit detail. In particular, in FIG. 2 the same reference numerals as in FIG. 1 are used to represent elements already mentioned above. It can be seen from FIG. 2 that power stage 72 is preferably in the form of two components 721 and 722 acting as a voltage regulator and as an output switch, that is, an actual power stage, respectively.

Impedance separator stage (of known type) indicated 79, has the function of permitting bidirectional connection of electrode 71 in the direction of output of the stimulation signal from power stage 72, and in the input direction towards the sensing channel.

The detailed diagram of FIG. 2 also shows that detector 78 is preferably in the form of a counter which is enabled to count by the output signal of comparator 76 and the count frequency of which is determined by a clock signal present on input line 781. The same drawing also shows that processing and timing unit 4 (also with a view to possible incorporation in a device which can be implanted) is preferably in the form of microprocessor 400 with associated read-only and random-access memories 401 and 402, respectively.

Since it has been demonstrated in the past that the variability of heart frequency during atrial fibrillation is connected with the vagal tonus, studies have recently been performed (see in particular the work "Post-ganglionic vagal stimulation of the atrioventricular node reduces ventricular rate during atrial fibrillation" by S. Garrigue et al, in Pace, April 1998, Vol. 21, No. 4, Part II, page 878) to evaluate the effect in reducing ventricular frequency during atrial fibrillation (induced in animals—rabbits) of a post-ganglionic vagal stimulation directly in contact with the atrioventricular node. It has been found that post-ganglionic vagal stimulation performed, in particular, with pulse trains in the manner described above, in contact with the atrioventricular node, can achieve an effective reduction in ventricular frequency during atrial fibrillation.

Naturally, the principle of the invention remaining the same, the details of construction and forms of embodiment may be varied widely with respect to those described and illustrated, without thereby departing from the scope of the present invention as defined by the following claims.

What is claimed is:

1. A method of stimulating the heart, comprising:
   providing a processing unit in electrical communication with a means for detecting atrial fibrillation and with first and second electrodes;
   implanting the electrodes in the heart;
   providing first electrical stimulation pulses to the heart from the first electrode above a stimulation threshold; and
   providing second electrical stimulation pulses to the heart from the second electrode below a stimulation threshold,
   wherein the second electrical stimulation pulses are delivered in response to the detection of atrial fibrillation.

2. The method of claim 1 wherein the first electrode is implanted in a location effective to stimulate at least one of an atrium and a ventricle of the heart.

3. The method of claim 1 wherein the second electrode is implanted in the region of the atrioventricular node of the heart.

4. The method of claim 1 wherein the second electrode is implanted in a region effective to inhibit propagation of pulses from an atrium of the heart to a ventricle of the heart.

5. The method of claim 1 further comprising providing a third electrode and providing third electrical stimulation pulses to the heart from the third electrode and wherein the first electrode is implanted in a location effective to stimulate an atrium of the heart, the third electrode is implanted in a location effective to stimulate a ventricle of the heart, and the second electrode is implanted in the region of the atrioventricular node of the heart.

6. The method of claim 1 further comprising providing a third electrode and providing third electrical stimulation pulses to the heart from the third electrode and wherein the first electrode is implanted in a location effective to stimulate an atrium of the heart, the third electrode is implanted in a location effective to stimulate a ventricle of the heart, and the second electrode is implanted in a region effective to inhibit propagation of pulses from an atrium of the heart to a ventricle of the heart.

7. The method of claim 2 wherein the second electrode is implanted in the region of the atrioventricular node of the heart.

8. The method of claim 2 wherein the second electrode is implanted in a region effective to inhibit propagation of pulses from an atrium of the heart to a ventricle of the heart.

9. The method of claim 1 wherein the second electrode further comprises a sensor for sensing the activity of the heart muscle.

10. The method of claim 1 wherein the processing unit is capable of varying at least one intensity parameter selected from the group of pulse amplitude, duration and frequency.

11. The method of claim 1 wherein the second electrode is configured to generate sub-threshold stimulation pulses in the form of individual pulses.

12. The method of claim 1 wherein the second electrode is configured to generate sub-threshold stimulation pulses synchronously according to spontaneous heart activity.

13. The method of claim 1 wherein the second electrode is configured to generate sub-threshold stimulation pulses in the form of repeated pulse trains.

14. The method of claim 1 wherein the second electrode is configured to generate sub-threshold stimulation pulses asynchronously according to spontaneous heart activity.

* * * * *